United States Patent [19]
Stammann et al.

[11] 4,370,275
[45] Jan. 25, 1983

[54] PROCESS FOR THE PREPARATION OF CARBONIC ACID ESTERS

[75] Inventors: Günter Stammann, Cologne; Robert Becker, Leverkusen; Johann Grolig, Leverkusen; Helmut Waldmann, Leverkusen, all of Fed. Rep. of Germany

[73] Assignee: Bayer Aktiengesellschaft, Leverkusen, Fed. Rep. of Germany

[21] Appl. No.: 250,363

[22] Filed: Apr. 2, 1981

[30] Foreign Application Priority Data

Apr. 26, 1980 [DE] Fed. Rep. of Germany ....... 3016187

[51] Int. Cl.³ .............................................. C07C 68/00
[52] U.S. Cl. .................................................. 260/463
[58] Field of Search ......................................... 260/463

[56] References Cited

U.S. PATENT DOCUMENTS 3,846,468 11/1974 Perrotti et al. ...................... 260/463
3,952,045 4/1976 Gaenzler et al. .................... 260/463

Primary Examiner—Henry R. Jiles
Assistant Examiner—Robert C. Whittenbaugh
Attorney, Agent, or Firm—Sprung, Horn, Kramer & Woods

[57] ABSTRACT

The invention relates to a process for the preparation of carbonic acid esters with high selectivity and under reaction conditions which permit high space/time yields, said process being one in which an alcohol is allowed to react with a mixture of molecular oxygen and carbon monoxide in the liquid phase in the presence of a catalyst system containing copper, chemically bonded oxygen, chemically bonded halogen and at least one nitrogen base.

8 Claims, No Drawings

PROCESS FOR THE PREPARATION OF CARBONIC ACID ESTERS

The present invention relates to the preparation of carbonic acid esters (carbonates) by reacting alcohols with mixtures of molecular oxygen and carbon monoxide in the liquid phase in the presence of a catalyst system which contains copper, chemically bonded oxygen, chemically bonded halogen and at least one nitrogen base.

It is already known that carbonic acid esters can be prepared from alcohols or phenols and phosgene, using stoichiometric amounts of a base. It is also possible to prepare carbonic acid esters from organic compounds containing hydroxyl groups and carbon monoxide under oxidising conditions in the presence of certain catalysts, (avoiding phosgene, which is difficult to handle), for example in accordance with the following equation:

$$2\text{ROH} + \text{CO} + \tfrac{1}{2}\text{O}_2 \xrightarrow{\text{catalyst}} (\text{RO})_2\text{CO} + \text{H}_2\text{O}$$

Thus, in U.S. Pat. No. 3,846,468 and U.S. Pat. No. Re. 29,338, it is stated that carbonic acid esters can be obtained in accordance with the above equation in the temperature range from $-20°$ C. to $+110°$ C. using stoichiometric amounts of catalyst, the catalyst preferably consisting of a mixture of a copper halide and an organic nitrogen base. However, because of the low reaction temperature in this process, it is difficult and expensive, from an industrial point of view, to remove the heat of reaction and to utilise it, and the space/time yields wich can be achieved for the organic carbonate are low.

DE-OS (German Published specification) No. 2,743,690 also describes a process of this type, in which copper salts are preferably used as catalysts. As can be seen from the examples of this DE-OS (German Published Specification), considerable amounts of catalyst are necessary for this process. This results in industrial problems when introducing the catalyst, separating off the catalyst and recycling the catalyst in this process. At these high catalyst concentrations, the process must be carried out at relatively low temperatures in order to achieve high selectivities and to be able to avoid corrosion.

A process has now been found for the preparation of carbonic acid esters from alcohols, carbon monoxide and molecular oxygen in the liquid phase, which is characterised in that it is carried out in the presence of a catalyst system which contains (a) copper and/or copper ions, (b) oxygen anions and/or anions containing oxygen, (c) halide ions, (d) one or more nitrogen bases and (e), optionally, other metal ions of metals from main group 2, of the lanthanide and/or actinide groups and/or of metals with atomic numbers of 25 to 30.

Starting materials which are employed for the process according to the invention are, on the one hand, carbon monoxide and molecular oxygen. Oxygen can be used in the pure form or in the form of mixtures with inert gases, such as nitrogen, and in particular in the form of air. The carbon monoxide and oxygen or oxygen-containing gas mixtures can be introduced in any desired sequence or as a mixture, but care must be taken that a procedure outside the explosion limits is followed.

Alcohols which can be employed as starting substances can be of the most diverse nature. Thus, for example, it is possible to employ linear or branched alkanols, cycloalkanols, alkenols, cycloalkenols, aralkyl alcohols (particularly mono- or bi-cyclic carbocyclic aryl lower alkanols and the like, it being possible for these to be monohydric or polyhydric (e.g. dihydric, trihydric etc.) and to contain 1 to 20 C atoms. The alcohols can contain substituents, such as oxygen, nitrogen, sulphur or halogen, for example one or more halogen, sulphoxide, sulphone, amine, amide, carbonyl and/or carboxylic acid ester groups. Preferably, one of the following alcohols is employed in the process according to the invention: methyl alcohol, ethyl alcohol, propanol, isopropanol, butanol, pentanol, hexanol, cyclohexanol, benzyl alcohol, ethylene glycol, diethylene glycol, propylene glycol, dipropylene glycol, glycerol, hexanetriol and the like and polyols of a higher functionality. Monohydric aliphatic alcohols (particularly alkanols) with 1 to 6 C atoms are preferably employed. Methanol, ethanol, 1-propanol and 2-propanol are very particularly preferred.

In general, the alcohols are employed in the process according to the invention in excess, that is to say in a weight ratio greater than 1:1, relative to the catalyst system. The alcohols are preferably employed in the process according to the invention in amounts such that they are in a weight ratio of 5:1 to 300:1, relative to the catalyst system. The alcohols are preferably employed in excess in relation to carbon monoxide, unreacted excess alcohol serving as the reaction medium. The molecular oxygen can be employed in less than the stoichiometric amount or in excess, relative to the alcohol. Preferably, an inert gas, such as nitrogen, is added or the process is carried out using air, the amounts being chosen such that a procedure outside the explosion range of the oxygen/carbon monoxide mixtures or the oxygen/alcohol mixtures is followed. If no inert gas is added, the amount of oxygen added is chosen such that explosive mixtures with carbon monoxide and the alcohol component are avoided. The molecular oxygen is preferably employed in the form of air or air/nitrogen mixtures.

The catalyst system to be used according to the invention contains: (a) copper and/or copper ions, (b) oxygen anions and/or anions containing oxygen, (c) halide ions, (d) one or more nitrogen bases and (e), optionally, other metal ions of metals of main group 2, from the lanthanide and/or actinide groups, and/or of metals with atomic numbers from 25 to 30.

Component (a) contained in the catalyst system to be used according to the invention can be employed as copper in any known oxidation stage. A catalytically active copper species, which can be in the O- to $+3$-valent form, can be formed therefrom under the reaction conditions. With regard to optimum selectivity of the carbonic acid ester formation, it is advantageous for copper to be introduced into the reaction predominantly in the $+2$ oxidation stage.

The catalyst system to be used according to the invention preferably contains ionic copper compounds. The cationic copper is preferably combined with one or more oxy-anions, hydroxy-nions or other oxygen-containing anions. Examples of copper compounds which can be employed according to the invention are copper-II oxide, copper I oxide, copper-II hydroxide, copper-II nitrate, copper-II hydroxycarbonate, copper-II hydroxynitrate, copper-II acetate, copper-II oxalate, copper-II citrate, copper-II acetylacetoniate, copper-II ethylate and copper naphthenate, it also being possible for several copper compounds to be employed. Copper-II oxide, copper-II hydroxycarbonate or copper-II hydroxide, by themselves or as many mixtures with one another, are particularly advantageously employed in the catalyst system to be used according to the invention. Using one or more of the abovementioned compounds, catalyst components (a) and (b) can be introduced.

Copper compounds which contain both oxygen and halogen are also suitable as catalyst components. In this case, copper-II oxychloride and atacamite ($Cu_2(OH)_3Cl$) are preferred. When such compounds are used as components of the catalyst system to be employed according to the invention, the addition of other copper ions or metal ions according to (e) can be disregarded. Catalyst components (a), (b) and (c) can be introduced by the abovementioned compounds.

Component (c) contained in the catalyst system to be used according to the invention can be the halide ions fluoride, chloride, bromide or iodide, by themselves or in combination with one another. In general, it is advantageous to use chloride as the halide ion of catalyst component (c). In this context, it is possible to employ chloride, for example, in the form of metal chlorides, metal oxychlorides or metal hydroxychlorides, and also in the form of ammonium chlorides. Copper ions and/or metal ions, according to catalyst component (e), in stable valency stages, or combinations thereof, can be chosen as the ions of opposite charge to the chloride ion. $Cu^{2+}$, $Fe^{2+}$, $Fe^{3+}$, $Co^{2+}$, $Ni^{2+}$, $Ca^{2+}$, $Mg^{2+}$ and caations of the lanthanide group are preferably used. If copper is not used as the metal ion, the metal ions are the other metal ions, corresponding to component (e), which may be contained in the catalyst system to be used according to the invention.

It is advantageous to employ some of the chloride in the form of an ammonium chloride, preferably as the hydrochloride of a nitrogen base and particularly preferably as the hydrochloride of an organic nitrogen base, and to employ the remainder as a chloride with the ions of opposite charge, corresponding to catalyst components (a) and/or (e).

Nitrogen bases which are suitable as catalyst component (d) include ammonia and monoacidic or polyacidic primary, secondary or tertiary alkylamines, cycloalkylamines, arylamines nd aralkylamines, it being possible for the nitrogen itself to be present bonded as part of an aliphatic or aromatic ring system or as a bridge atom in a cyclic or polycyclic ring system. Such nitrogen bases, others than ammonia, may contain in general 1 to 700 C atoms. Preferably used are nitrogen bases containing up to 20 C atoms, therein included are carbocyclic or heterocyclic amines with 3 to 18 carbon atoms bonded in at least one ring system. Suitable nitrogen bases with higher numbers of C-atoms are for instance oligomerics of etlylenimine and cocondensation products of epoxides and imines. Substituted nitrogen bases may also be suitable. Examples which may be mentioned of suitable organic nitrogen bases are: n-butylamine, diethylamine, triethylamine, hexamethylenediamine, dicyclohexylamine, aniline, 2,4-diaminotoluene, 3-aminopropyl ethyl ether, 2-methylpiperidine, 1-amino-2-methylindoline, pyridine, 2,4,6-trimethylpyridine, quinoline, 6-chloro-2-methylquinoline, 3,6-dinitro-9-H-carbazole, 4-phenyl-morpholine, 10H-phenothiazine, 1,4-diazabicyclo[2.2.2]octane and 1-aza-4,6-dioxabicyclo[3.3.0]octane, aliphatic amines and hetero-aromatics containing nitrogen, such as pyridine, preferably being employed. Other suitable nitrogen bases are benzimidazole, benzotriazole, 2-(5-aminopentyl)benzimidazole and 1,2-pentamethylene-benzimidazole. Catalyst component (d) can be introduced in the above-mentioned way.

For carrying out the process according to the invention, it is advantageous to employ one or more of the nitrogen bases as hydrochlorides, or complexed with catalyst components (a) and/or, optionally, (e). Examples of such hydrochlorides and complexes are: pyridine hydrochloride, dipyridino-copper-II hydroxychloride, dipyridino-copper-II chloride, dipyridinocobalt-II chloride and ammonium tetrachlorocuprate-II. If such a compound is employed, it is possible to introduce catalyst components (a), (c) and (d), and, optionally, also (b) and (e), with one compound.

For the process according to the invention, it is advantageous to employ catalyst components (a) to (d) and, optionally, (e) in certain proportions relative to one another in order to achieve optimum activity and selectivity of the catalyst system.

The halide content of the catalyst system to be used according to the invention is preferably established such that, for example by suitable combination of the individual catalyst components, the ratio of total halide to total metal, expressed in gram-atoms, is 0.5:1 to 2:1, in particular 0.8:1 to 1.4:1. Choride contents which are introduced in the form of a hydrochloride, and preferably in the form of pyridine hydrochloride, are preferably chosen such that the ratio of this chloride content to the total metal, expressed in gram-atoms, is 0.1:1 to 1:1, preferably 0.3:1 to 0.8:1.

The nitrogen base (catalyst component (d)), is advantageously employed in an amount such that the molar ratio of the nitrogen base to the total metal of the catalyst system is 0.1:1 to 1.4:1, preferably 0.3:1 to 1.2:1. This ratio is independent of whether the nitrogen base is employed in the free form or as a complex with one of the suitable metal salts or as ammonium chloride or a hydrochloride.

The oxidic or oxygen-containing catalyst component according to (b) is an essential component of the catalyst system. It is preferably employed in the form of a copper compound. In relation to the other metal compounds present as metal halides or as metal halide complexes, catalyst component (b) is preferably employed in a molar ratio of 0.5:1 to 3:1, preferably 1.5:1 to 2.2:1. If oxy-halogen or hydroxy-halogen compounds of copper are used for this, catalyst components (a) to (c) can be introduced by these compounds. It is then possible to add further copper ions and/or other metal ions according to (e), but is not absolutely necessary.

Of the various possibilities for the preparation of a catalyst system, which can be used according to the invention, from the abovementioned components, some combinations are particularly advantageous for the process according to the invention if the composition is to be chosen according to the abovementioned ratios. These preferred combinations include the following: $CuCo_3.Cu(OH)_2$, $CuCl_2$ and pyridine hydrochloride; $CuCO_3.Cu(OH)_2$, $CoCl_2$ and pyridine hydrochloride; $Cu_2OCl_2$ and pyridine hydrochloride; $Cu_2(OH)_3Cl$ and pyridine hydrochloride; $Cu(OH)Cl.2$ pyridine, $CuCl_2.2$ pyridine, $CuCl_2.2H_2O$ and $Cu_2(OH)_3Cl$. Mixtures of the particularly advantageous combinations mentioned are, of course, also suitable for the process according to the invention.

A particular advantage of the catalyst system to be used according to the invention is that, after letting down and cooling the reaction mass, the catalyst mixture precipitates, if necessary after driving off some of the solvent or excess alcohol. The precipitated catalyst mixture can be recycled and is still catalytically active. If exclusively copper compounds are employed as metal components in the catalyst system according to the invention, the catalyst mixture can contain, after the reaction, varying amounts of $CuCl_2.2H_2O$, $Cu_2(OH)_3Cl$ (atacamite), and for instance $CuCl_2.2$ pyridine and $Cu(OH)Cl.2$ pyridine—if pyridine is used as the nitrogen base—as the main constituents depending on the concentration of the starting components.

If pyridine or pyridine hydrochloride is added as the nitrogen base in the amounts mentioned as preferred, the product solution may contain pyridine, but if at all only traces thereof. This does not usually interfere with working up of the product by distillation, after the catalyst has been separated off. In this case, the pyridine employed is present almost exclusively as pyridine bonded as a complex with copper compounds or, if appropriate, with metal compounds according to catalyst component (e), and, in this form, is also a catalytically active catalyst constituent.

It is in general advantageous, before recycling the catalyst, to separate off a proportion of, for example, 5 to 30% by weight, preferably 10 to 15% by weight, and to remove the water of reaction chemically and/or physically bonded therein, for example, by heat treatment. Preferably, fresh catalyst system to be used according to the invention, or catalyst system to be used according to the invention which is regenerated, for example by heat treatment, is then added to the recycled catalyst in an amount corresponding to the amount of catalyst removed.

The catalyst system to be used according to the invention enables carbonic acid esters to be prepared in high selectivity and under reaction conditions which permit high space/time yields and, if appropriate, industrial utilisation of the heat of reaction from the highly exothermic reaction. For example, in the process according to the invention, the heat of reaction obtained at a relatively high temperature level can be utilised to distil off the solvent or the excess alcohol.

The total amount of catalyst in the process according to the invention is preferably 0.5 to 8% by weight, relative to the total starting material, including solvent.

In the process according to the invention, it is particularly advantageous that it is also possible to achieve high space/time yields and selectivities with very small amounts of metal compounds according to components (a) and/or, if appropriate, (e). It is surprising that the corrosion problems known in the case of copper halides in connection with customary reactor materials do not occur with the catalyst system to be used according to the invention. Suitable reactor materials for the process according to the invention are, for example, those according to DIN 17 44, with the designations 1.4571, 1.4577 and 1.4439, as well as alloys based on nickel, for example the material with the designation Ni MO 16 Cr 16 Ti.

The process according to the invention for the preparation of carbonic acid esters can be carried out discontinuously or continuously.

The reaction can be carried out by a procedure in which the alcohol component, with the catalyst system to be used according to the invention, is initially reacted with carbon monoxide in a first reaction step, and the mixture is then reacted with molecular oxygen in a second reaction step. In this procedure, the carbonic acid ester is at most formed in stoichiometric amounts, relative to the metal in the catalyst system according to the invention.

The reaction according to the invention can be carried out in the presence or absence of a solvent. In general, the alcohol, which is preferably employed in excess, serves as the solvent. However, it is also possible to use inert solvents, which can be present to the extent of 80% by weight of the entire reaction batch.

Solvents which can be used are solvents which are inert towards the reactants and the catalyst system under the reaction conditions, for example aromatic, cycloaliphatic and aliphatic hydrocarbons, which are preferably substituted by halogen, such as chlorobenzene, dichlorobenzene, trichlorobenzene, chloronaphthalene, chlorocyclohexane, methylene chloride, carbon tetrachloride, tetrachloroethane, trichlorofluoroethane and similar compounds.

The reaction temperature for the process according to the invention can in general be between 50° and about 250° C. The reaction is preferably carried out between 110° and 220° C., and particulrly advantageously in the range from 140° to 200° C. The pressure must be chosen such that the presence of a liquid phase is always ensured. It can in general be less than 250 bars, at the reaction temperature, and the reaction is preferably carried out in the range between 50 and 200 bars.

The process according to the invention is illustrated in more detail by the following examples, without being restricted thereto.

EXAMPLES

Examples 1–8

(Examples 1 and 2 are comparison examples to Examples 3 to 8, since Examples 1 and 2 contain no catalyst component according to (b))

In each case 96.86 to 99.0% by weight of ethanol (200 g) and the catalyst components according to Table 1 were initially introduced into a 0.7 l high-grade steel autoclave. After flushing with nitrogen, first 100 bars of carbon monoxide and then 25 bars of air were forced in at room temperature. The reaction mixture was heated to 180° C. for one hour, whilst stirring. After cooling, the autoclave was let down and the reaction mass was reacted in the same manner a second time, with a freshly forced-in carbon monoxide/air mixture. After renewed cooling and letting down, the reaction solution was in each case analysed quantitatively by gas chromatography. Samples of the product gases contained on average 1 to 2% by volume of $CO_2$.

TABLE 1

| Example No. | Catalyst (% by weight) (Py = pyridine) | Conversion (%) (relative to ethanol) | Diethyl carbonate Selectivity (mol %) | Diethyl carbonate g of yield per g of catalyst |
|---|---|---|---|---|
| 1 | $CuCl_2$ (1.94) Py (1.20) | 11.3 | 92.7 | 4.2 |
| 2 | $Cu_2Cl_2$ (1.47) Py (0.58) | 7.6 | 98.0 | 4.5 |
| 3 | CuO (0.97), $CuCl_2$ (0.97), Py.HCl (0.97) | 12.2 | 98.5 | 5.1 |
| 4 | $Cu_2OCl_2$ (1.94), Py.HCl (0.97) | 11.7 | 98.0 | 4.9 |

TABLE 1-continued

| Example No. | Catalyst (% by weight) (Py = pyridine) | Conversion (%) (relative to ethanol) | Diethyl carbonate Selectivity (mol %) | g of yield per g of catalyst |
|---|---|---|---|---|
| 5 | Atacamite (1.37), Py.HCl (0.49) | 9.1 | 97.0 | 5.9 |
| 6 | CuCl$_2$.2 Py (0.1), atacamite (0.3) Cu(OH)Cl.2 Py (0.6) | 6.4 | 99.1 | 8.1 |
| 7 | CuCl$_2$.2 Py (0.7), atacamite (0.7), Py (0.1) | 6.7 | 96.0 | 5.5 |
| 8 | (NH$_4$)$_2$CuCl$_4$ (1.0), CuO (1.0) | 13.6 | 85.0 | 7.4 |

EXAMPLE 9

A mixture of 97.1% by weight (200 g) of ethanol and in each case 0.97% by weight of the catalyst components copper-II oxide, copper-II chloride (anhydrous) and pyridine hydrochloride was twice reacted, in a 0.7 l high-grade steel autoclave, with gas mixtures of 100 bars of carbon monoxide and 20 bars of air, in each case at 120° C. for 2 hours. The ethanol was converted into diethyl carbonate to the extent of 7.6%, with a selectivity of 99.9%.

EXAMPLE 10

The procedure followed was as in Example 9, but the catalyst system consisted of 0.54% by weight of copper-II oxide, 0.88% by weight of copper-II chloride (anhydrous) and 1.07% by weight of aniline hydrochloride. The ethanol was converted into diethyl carbonate to the extent of 5.8%, with a selectivity of 99.6%.

EXAMPLES 11-19

The procedure followed was as given in Example 1, but the catalyst system consisted of 0.97% by weight of copper-II oxide, 0.97% by weight of pyridine hydrochloride and 0.68 to 1.20% by weight of a metal chloride. The results thereby obtained can be seen from Table 2.

TABLE 2

| Example No. | Metal chloride (% by weight) | Conversion (%) (relative to ethanol) | Selectivity (%) Diethyl carbonate (relative to ethanol) |
|---|---|---|---|
| 11 | MgCl$_2$ (0.68) | 7.2 | 98.9 |
| 12 | CaCl$_2$ (0.83) | 8.9 | 97.9 |
| 13 | LaCl$_3$ (1.20) | 8.8 | 98.5 |
| 14 | MnCl$_2$ (0.92) | 7.6 | 97.7 |
| 15 | FeCl$_2$ (0.97) | 10.2 | 94.9 |
| 16 | FeCl$_3$ (0.78) | 11.1 | 90.7 |
| 17 | CoCl$_2$ (0.97) | 9.6 | 99.3 |
| 18 | NiCl$_2$ (0.97) | 9.4 | 98.0 |
| 19 | ZnCl$_2$ (0.97) | 6.7 | 98.2 |

EXAMPLES 20-23

These examples show that, with the catalyst system used according to the invention, increasing yields of carbonate are obtained by increasing the amount of oxygen available.

A mixture of 97.1% by weight (200 g) of ethanol and in each case 0.97% by weight of the catalyst components copper-II oxide, copper-II chloride (anhydrous) and pyridine hydrochloride was reacted, in a 0.7 l high-grade steel autoclave, with gas mixtures of 100 bars of carbon monoxide and 20 bars of air in 1 to 5 reaction cycles, in each case at 180° C. for 2 hours. The results can be seen from Table 3.

TABLE 3

| Example No. | Number of reaction cycles | Yield of diethyl carbonate (% of theory) |
|---|---|---|
| 20 | 1 | 9.3 |
| 21 | 2 | 12.0 |
| 22 | 3 | 16.8 |
| 23 | 5 | 25.1 |

EXAMPLES 24-26

The procedure followed was as in Example 3, but instead of ethanol, the alcohol methanol, 1-propanol or 2-propanol was employed. The results thereby obtained can be seen from Table 4.

TABLE 4

| Example No. | Alcohol | Yield of dialkyl carbonate (% of theory) |
|---|---|---|
| 24 | methanol | 7.7 |
| 25 | 1-propanol | 10.6 |
| 26 | 2-propanol | 1.9 |

EXAMPLES 27 AND 28

97.1% by weight (200 g) of ethanol and a catalyst mixture consisting of 0.97% by weight of copper-II chloride, 0.97% by weight of pyridine hydrochloride and 0.97% by weight of a further component were reacted twice, in a 0.7 l high-grade steel autoclave, with gas mixtures of 100 bars of carbon monoxide and 20 bars of air, in each case at 180° C. for 1 hour. The results can be seen from Table 5.

TABLE 5

| Example No. | additional component | yield of diethyl carbonate (%), relative to ethanol |
|---|---|---|
| 27 | copper-II acetate hydrate | 8.0 |
| 28 | copper-II hydroxycarbonate | 9.8 |

What is claimed is:
1. Process for the preparation of carbonic acid esters which comprises reacting an alcohol, carbon monoxide and molecular oxygen in the liquid phase, in the presence of a catalyst system which contains
   (a) copper and/or copper ions,
   (b) one or more anions selected from oxide anion, hydroxide anion and carbonate anion,
   (c) halide ions,
   (d) one or more nitrogen bases and
   (e) optionally, other metal ions of metals from main group 2, of the lanthanide and/or actinide groups and/or of metals with atomic numbers of 25 to 30,
these components (a)–(e) being contained in amounts corresponding to
   a ratio of total halide to total metal ranging from 0.5:1 to 2:1 expressed ingram-atoms,
   a molar ratio of total nitrogen base to total metal ranging from 0.1:1 to 1.4:1,
   a molar ratio of anions corresponding to component (b) to metal halides or metal halide complexes from 0.5:1 to 3:1, and a ratio of the optionally used other metal ions to copper or copper ions ranging up to 0.625:1 expressed in gram-atoms.

2. Process according to claim 1, characterised in that a monohydric aliphatic alcohol with 1 to 6 C atoms is employed as the alcohol.

3. Process according to claim 1 or 2, characterised in that the alcohol is employed in a weight ratio of 5:1 to 300:1, relative to the catalyst system.

4. Process according to claim 1, characterised in that chloride is used as catalyst component (c).

5. Process according to claim 4, characterised in that some of the chloride is employed in the form of an ammonium chloride and the remainder is employed as a chloride together with ions of opposite charge which correspond to catalyst components (a) and/or (e).

6. Process according to claim 1 or 5, characterised in that catalyst component (d) is a nitrogen base with 1 to 700 C atoms.

7. Process according to claim 1, characterised in that the catalyst is re-used, after a proportion of 5 to 30% by weight has been separated off and the water of reaction bonded therein has been removed.

8. Process according to claim 1, characterised in that it is carried out between 50° and 250° C. and under less than 250 bars.

* * * * *